(12) United States Patent
Kim et al.

(10) Patent No.: US 11,247,975 B2
(45) Date of Patent: Feb. 15, 2022

(54) PROCESS FOR PURIFYING AN ALKYLENE OXIDE COMPOSITION

(71) Applicant: SK PICGLOBAL CO., LTD., Ulsan (KR)

(72) Inventors: Hanna Kim, Ulsan (KR); Doojin Lee, Gyeonggi-do (KR); Eun Su Lee, Gyeongsangnam-do (KR); Taechan Ha, Ulsan (KR); Dong Kyun Noh, Gyeonggi-do (KR); Soo Hyun Park, Ulsan (KR); Sungho Kim, Ulsan (KR)

(73) Assignee: SK PICGLOBAL CO., LTD, Ulsan (KR)

( * ) Notice: Subject to any disclaimer, the term of this patent is extended or adjusted under 35 U.S.C. 154(b) by 0 days.

(21) Appl. No.: 16/313,782

(22) PCT Filed: Jul. 16, 2018

(86) PCT No.: PCT/KR2018/008015
§ 371 (c)(1),
(2) Date: Dec. 27, 2018

(87) PCT Pub. No.: WO2019/231044
PCT Pub. Date: Dec. 5, 2019

(65) Prior Publication Data
US 2021/0246111 A1 Aug. 12, 2021

(30) Foreign Application Priority Data

May 29, 2018 (KR) .................. 10-2018-0060946

(51) Int. Cl.
*C07D 301/32* (2006.01)
*B01J 29/035* (2006.01)
*C07D 303/04* (2006.01)

(52) U.S. Cl.
CPC .......... *C07D 301/32* (2013.01); *B01J 29/035* (2013.01); *C07D 303/04* (2013.01)

(58) Field of Classification Search
CPC ..... C07D 301/32; C07D 303/04; B01J 29/035
USPC ........................................................ 549/541
See application file for complete search history.

(56) References Cited

U.S. PATENT DOCUMENTS

| 3,335,547 A | 8/1967 | Garrett et al. |
| 4,772,732 A | 9/1988 | Huang et al. |
| 2006/0189833 A1* | 8/2006 | Powell .................... C07C 45/79 568/620 |

FOREIGN PATENT DOCUMENTS

| CN | 106117165 A | 11/2016 |
| CN | 106397362 A * | 2/2017 |
| DE | 69616895 T2 | 1/1997 |
| JP | 08-283253 | 10/1996 |
| JP | 2003160573 | 6/2003 |
| JP | 2012-224608 | 11/2012 |
| KR | 10-2001-0111573 | 12/2001 |
| KR | 1020070100912 | 10/2007 |
| KR | 10-1433626 | 9/2014 |
| WO | 2009/105252 | 8/2009 |

OTHER PUBLICATIONS

Sun, N. et al., Investigations on the mechanism, kinetics and isotherms of ammonium and humic acid co-adsorption at low temperature by 4A-molecular sieves modified from attapulgite, RSC Advances, 2017, p. 17095-17106, The Royal Society of Chemistry.
Office Action issued by the Hungarian Patent Office dated Oct. 14, 2019.
Office Action issued by German Patent dated Jan. 16, 2020.
Office Action issued by the Korean Intellectual Property Office dated Aug. 21, 2018.
Wikipedia: Molekularsieb, Apr. 29, 2018, URL: https://en.wikipedia.org/wiki/Molecular_sieve.
Office Action issued to the corresponding German Patent Application No. 11 2018 000 071.0, dated Jul. 1, 2021.

* cited by examiner

*Primary Examiner* — Taylor V Oh
(74) *Attorney, Agent, or Firm* — IP & T Group LLP

(57) ABSTRACT

Embodiments provide a process for purifying an alkylene oxide composition, which comprises (1) obtaining a crude alkylene oxide composition comprising an ionic component; (2) passing the crude alkylene oxide composition through a molecular sieve; and (3) obtaining a purified alkylene oxide composition. A purified alkylene oxide composition suitable for a subsequent process can be obtained.

15 Claims, No Drawings

PROCESS FOR PURIFYING AN ALKYLENE OXIDE COMPOSITION

This application is a national stage application of PCT/KR2018/008015 filed on Jul. 16, 2018, which claims priority of Korean patent application number 10-2018-0060946 filed on May 29, 2018. The disclosure of each of the foregoing applications is incorporated herein by reference in its entirety.

TECHNICAL FIELD

Embodiments relate to a process for purifying an alkylene oxide composition by removing an ionic component generated in the production of an alkylene oxide.

BACKGROUND ART OF THE INVENTION

Alkylene oxides are used as important intermediates in the chemical industry. Alkylene oxides are produced by various processes. Different byproducts may be generated depending on what reactants, catalysts, solvents, and the like are used.

For example, propylene oxide has been mainly produced by the process through a hydrochlorination route and the dual production process (i.e., a process of producing a styrene monomer or methyl tertiary butyl ether together with propylene oxide). However, the process through a hydrochlorination route has been gradually avoided due to the contamination problem. The dual production process also involves difficulties in the new establishment or expansion of facilities due to the limited usage of the byproducts. Thus, in recent years, studies have been made on new processes for producing propylene oxide.

According to a new production process, propylene is epoxidized with hydrogen peroxide as an oxidizing agent under the action of a titanium compound catalyst, thereby producing a propylene oxide composition. This production process is advantageous in that the process is simple, capable of consuming a low level of energy, and environmentally friendly.

However, this process is disadvantageous in that the propylene oxide composition thus prepared contains an impurity that may affect a subsequent process for producing a polyol or the like. Thus, studies have continued on what kind of impurities are generated and how to selectively remove these impurities.

DISCLOSURE OF THE INVENTION

Technical Problem to be Solved

Embodiments aim to provide a purified alkylene oxide composition suitable for a subsequent process by selectively removing an ionic component, which is not necessary for the subsequent process, from the byproducts of alkylene oxide produced by the new process.

Solution to the Problem

The process for purifying an alkylene oxide composition according to an embodiment comprises (1) obtaining a crude alkylene oxide composition comprising an ionic component; (2) passing the crude alkylene oxide composition through a molecular sieve; and (3) obtaining a purified alkylene oxide composition.

Advantageous Effects of the Invention

According to the process for purifying an alkylene oxide composition according to the embodiments, a purified alkylene oxide composition suitable for a subsequent process can be obtained.

DETAILED DESCRIPTION FOR CARRYING OUT THE INVENTION

Hereinafter, the present invention will be described in detail with reference to the embodiments. The embodiments are not limited to those described below. Rather, they may be modified into various forms as long as the gist of the invention is not altered.

In this specification, when a part is referred to as "comprising" an element, it is to be understood that the part may comprise other elements as well.

Further, all numbers and expression related to the quantities of components, reaction conditions, and the like used herein are to be understood as being modified by the term "about," unless otherwise indicated.

Embodiments aim to provide a purified alkylene oxide composition suitable for a subsequent process.

The process for purifying an alkylene oxide composition according to an embodiment comprises (1) obtaining a crude alkylene oxide composition comprising an ionic component; (2) passing the crude alkylene oxide composition through a molecular sieve; and (3) obtaining a purified alkylene oxide composition.

First, in order to purify an alkylene oxide composition according to an embodiment, a crude alkylene oxide composition comprising an ionic component is obtained (step (1)).

A crude alkylene oxide composition refers to a composition immediately after being produced by a process for producing an alkylene oxide. The composition comprises an ionic component or the like, which is not necessary for a subsequent process.

The crude alkylene oxide composition may comprise an alkylene oxide, an ionic component, a nonionic component, and a solvent.

The crude alkylene oxide composition comprises an ionic component.

The ionic component may comprise a cationic component and an anionic component.

Specifically, the cationic component may be at least one selected from the group consisting of $NH_2^+$, $NH_4^+$, and molecular sieves having them as a functional group. For example, the cationic component may comprise $NH_4^+$. As another example, the cationic component may comprise $NH_2^+$ and $NH_4^+$. For example, the cationic component may be composed of $NH_4^+$, but it is not limited thereto.

The ionic component comprises $NH_4^+$, and the content of $NH_4^+$ contained in the crude alkylene oxide composition is 0.1 to 5 ppm. Specifically, the ionic component comprises $NH_4^+$, and the content of $NH_4^+$ contained in the crude alkylene oxide composition is 0.1 to 3 ppm, 0.1 to 2.5 ppm, 0.3 to 2 ppm, or 0.5 to 1.5 ppm, but it is not limited thereto.

In addition, the anionic component may be at least one selected from the group consisting of $NO_2^-$, $NO_3^-$, and molecular sieves having them as a functional group. For example, the anionic component may comprise $NO_2^-$. As another example, the anionic component may comprise $NO_2^-$ and $NO_3^-$. For example, the anionic component may be composed of $NO_2^-$, but it is not limited thereto.

The ionic component comprises $NO_2^-$, and the content of $NO_2^-$ contained in the crude alkylene oxide composition is 0.1 to 5 ppm. The ionic component comprises $NO_2^-$, and the content of $NO_2^-$ contained in the crude alkylene oxide composition is 0.1 to 3 ppm, 0.1 to 1 ppm, or 0.25 to 0.75 ppm, but it is not limited thereto.

The ionic component may comprise a nitrogen-containing ionic component.

For example, the ionic component may comprise at least one selected from the group consisting of $NH_2^+$, $NH_4^+$, $NO_2^-$, and $NO_3^-$. Alternatively, the ionic component may be composed of at least one selected from the group consisting of $NH_2^+$, $NH_4^+$, $NO_2^-$, and $NO_3^-$.

The ionic component comprises 30 to 90% by weight of the cationic component based on the total weight of the ionic component. Specifically, the ionic component may comprise 40 to 90% by weight, 50 to 90% by weight, or 50 to 80% by weight, of the cationic component based on the total weight of the ionic component. More specifically, the ionic component may comprise 60 to 80% by weight of the cationic component based on the total weight of the ionic component, but it is not limited thereto.

The crude alkylene oxide composition may comprise a nonionic component in addition to the ionic component.

For example, the nonionic component may comprise an amine-based component.

Specifically, the amine-based component may comprise at least one selected from the group consisting of diisopropylamine, diethylamine, trimethylamine, diethanolamine, dimethylethylamine, methyldiethanolamine, and monoisopropylamine.

In addition, the crude alkylene oxide composition may comprise a solvent.

Specifically, the solvent may comprise at least one selected from the group consisting of water, methanol, acetaldehyde, propionaldehyde, methyl formate, and dimethoxymethane.

For example, the crude alkylene oxide composition may comprise dimethoxy methane (DMM) and methyl formate (MF). The content of dimethoxy methane (DMM) and methyl formate (MF) may be 10 to 3,000 ppm, 10 to 1,000 ppm, 10 to 500 ppm, or 20 to 100 ppm, but it is not limited thereto.

The crude alkylene oxide composition in the above step (1) has a controlled polymerization rate (CPR) of 0.2 to 20. Specifically, the crude alkylene oxide composition may have a controlled polymerization rate (CPR) of 0.2 to 10, 0.2 to 5, 0.2 to 2, 0.5 to 3, 0.5 to 2, or 0.8 to 1.5, but it is not limited thereto.

The controlled polymerization rate (CPR) refers to an index that indicates the amount of a basic substance in an alkylene oxide composition. It is a value measured according to the test method of ASTM D6437, wherein 30 g of an alkylene oxide composition is mixed with 100 ml of methanol, and the amount of hydrochloric acid (concentration: 0.001 N) for neutralization titration is measured.

If the CPR of the crude alkylene oxide composition in the above step (1) is outside the above range, it is difficult to control the reactivity in the production of a downstream product using the same as a raw material, as well as the CPR value of the product thus produced falls outside from the CPR specification of the product. Thus, the CPR of the crude alkylene oxide composition must be maintained within the above range. Specifically, it is more advantageous to maintain the CPR value of the crude alkylene oxide composition to be 2.0 or less to the maximum.

Specifically, since the amount of the cationic impurities in the ionic impurities is relatively larger than that of the anionic impurities, the cationic impurities remaining after neutralization of the impurities may be a factor of increasing the CPR value of the crude alkylene oxide composition.

The crude alkylene oxide composition in the above step (1) has a basicity of 1 to 40. Specifically, the crude alkylene oxide composition may have a basicity of 2 to 40, 2 to 20, 0.4 to 10, or 0.4 to 7, but it is not limited thereto.

Specifically, since the amount of the cationic impurities in the ionic impurities is relatively larger than that of the anionic impurities, the cationic impurities remaining after neutralization of the impurities may be a factor of increasing the basicity of the crude alkylene oxide composition.

The crude alkylene oxide composition in the above step (1) has a content of N of 0.2 to 10 ppm. Specifically, the crude alkylene oxide composition has a content of N of 0.2 to 7 ppm, 0.2 to 5 ppm, 0.2 to 3 ppm, or 0.2 to 2 ppm. More specifically, the crude alkylene oxide composition may have a content of N of 0.5 to 1.8 ppm, 1.0 to 1.8 ppm, or 1.2 to 1.8 ppm, but it is not limited thereto.

If the content of N of the crude alkylene oxide composition in the above step (1) is maintained at a high level, it may cause odor in the downstream product that uses the same as a raw material. Thus, the content of N of the crude alkylene oxide composition is preferably maintained as low as possible.

The factors that increase the content of N of the crude alkylene oxide composition are the components that contain N in the ionic component, the nonionic component, and the solvent as described above.

The alkylene oxide may be ethylene oxide, propylene oxide, butylene oxide, or the like. Specifically, the alkylene oxide may be propylene oxide.

The crude alkylene oxide composition may be passed through a bead section after the step (1) and before the following step (2).

The bead section comprises a plurality of beads having an average diameter of 1 to 5 mm. Specifically, the bead section may comprise a plurality of beads having an average diameter of 1.5 to 4 mm or 2 to 3 mm, but it is not limited thereto.

The number of beads contained in the bead section per unit volume is 100 to 100,000/liter. Specifically, the number of beads contained in the bead section per unit volume may be 1,000 to 80,000/liter, 5,000 to 70,000/liter, 10,000 to 50,000/liter, or 15,000 to 40,000/liter, but it is not limited thereto.

In addition, the space velocity at which the crude alkylene oxide composition is passed through the bead section is greater than 0 to 10 $h^{-1}$. Specifically, the space velocity at which the crude alkylene oxide composition is passed through the bead section may be 0.2 to 5 $h^{-1}$, 0.2 to 3 $h^{-1}$, 0.2 to 2 $h^{-1}$, 0.5 to 2 $h^{-1}$, or 0.8 to 1.5 $h^{-1}$, but it is not limited thereto.

The beads contained in the bead section may comprise an inactive material made of silicalite as a raw material.

The bead section serves to induce even dispersion of the crude alkylene oxide composition before it is fed to a molecular sieve in the downstream.

Next, the crude alkylene oxide composition is passed through a molecular sieve (step (2)).

The molecular sieve may be a zeolite-based molecular sieve. Specifically, the molecular sieve may have a structure selected from the group consisting of zeolite A, zeolite X, zeolite beta, zeolite Y, zeolite L, and ZSM-12.

The molecular sieve collectively refers to silicon aluminum oxides and may be in an octagonal geometric structure that has an inlet of fine holes composed of oxygen atom rings and intersecting other holes bent at regular intervals between the holes, but it is not limited thereto.

In such event, the size of the pores of the molecular sieve is greater than 2.3 Å to less than 10 Å. Specifically, the size of the pores of the molecular sieve may be 3 Å to less than 10 Å, 3 Å to 7.5 Å, 3 Å to 5 Å, 3.5 to 4.5 Å, 3.8 to 4.2 Å, or 3.9 to 4.1 Å, but it is not limited thereto.

In addition, the shape of the pores of the molecular sieve may be octagonal. Specifically, the molecular sieve has micropores in an octagonal shape, and commercialized products have a spherical shape of about 2 mm in which molecular sieves are physically combined.

The molecular sieve can selectively adsorb smaller impurities than the micropores in an octagonal shape. Alternatively, the negative charge (i.e., acid point) of the zeolite series itself of the molecular sieve can adsorb the cationic component present in the crude alkylene oxide composition.

The space velocity at which the crude alkylene oxide composition is passed through the molecular sieve is greater than 0 to 10 $h^{-1}$. Specifically, the space velocity at which the crude alkylene oxide composition is passed through the molecular sieve may be 0.2 to 5 $h^{-1}$, 0.2 to 3 $h^{-1}$, 0.2 to 2 $h^{-1}$, 0.5 to 2 $h^{-1}$, or 0.8 to 1.5 $h^{-1}$, but it is not limited thereto.

Next, a purified alkylene oxide composition is obtained (step (3)).

The purified alkylene oxide composition comprises an ionic component that comprises a cationic component and an anionic component.

In such event, the kind of the ionic component is as described in the above step (1).

In addition, the purified alkylene oxide composition may comprise a nonionic component and a solvent in addition to the ionic component. They are as described in the above step (1).

If the purified alkylene oxide composition comprises an ionic component that comprises a cationic component and an anionic component, the ionic component comprises 10 to 70% by weight of the cationic component based on the total weight of the ionic component. Specifically, the ionic component comprises 20 to 70% by weight, 30 to 70% by weight, 40 to 60% by weight, or 45 to 55% by weight, of the cationic component based on the total weight of the ionic component, but it is not limited thereto.

For example, the purified alkylene oxide composition comprises $NH_4^+$, and the content of $NH_4^+$ contained in the purified alkylene oxide composition is 0.05 to 2.5 ppm. Specifically, the content of $NH_4^+$ contained in the purified alkylene oxide composition may be 0.1 to 2 ppm, 0.1 to 1 ppm, 0.2 to 0.8 ppm, 0.2 to 0.6 ppm, or 0.4 to 0.6 ppm, but it is not limited thereto.

That is, a significant amount of the cationic component such as $NH_4^+$ contained in the crude alkylene oxide composition can be removed as the composition is passed through the molecular sieve.

In addition, the purified alkylene oxide composition comprises $NO_2^-$, and the content of $NO_2^-$ contained in the purified alkylene oxide composition is 0.1 to 5 ppm. Specifically, the content of $NO_2^-$ contained in the purified alkylene oxide composition may be 0.1 to 3 ppm or 0.25 to 0.75 ppm, but it is not limited thereto.

The purified alkylene oxide composition in the above step (3) has a CPR of 0 to 2. Specifically, the purified alkylene oxide composition may have a CPR of 0 to 1.5, 0 to 1.2, 0 to 0.8, 0 to 0.5, 0.1 to 0.5, 0.1 to 0.3, or 0.1 to 0.2, but it is not limited thereto.

The definition of the CPR is as described in the above step (1).

If the CPR of the purified alkylene oxide composition in the above step (3) is within the above range, it is advantageous in that the reactivity in the production of a downstream product using the same as a raw material is easily controlled, as well as the low CPR value of the product thus produced meets the CPR specification of the product.

The purified alkylene oxide composition in the above step (3) has a basicity of 0 to 4. Specifically, the purified alkylene oxide composition may have a basicity of 0 to 3, 0 to 2.4, 0 to 1.6, or 0 to 1.0, but it is not limited thereto.

The purified alkylene oxide composition in the above step (3) has a content of N of 0.1 to 5 ppm. More specifically, the purified alkylene oxide composition may have a content of N of 0.1 to 3 ppm, 0.1 to 2 ppm, 0.2 to 1.5 ppm, or 0.4 to 1.1 ppm, but it is not limited thereto.

If the content of N of the purified alkylene oxide composition in the above step (3) is within the above range, it is advantageous in that the odor in the downstream product that uses the same as a raw material is reduced to a level of odor in a downstream product that uses an alkylene oxide produced by other processes such as the process through a hydrochlorination route and the dual production process.

Hereinafter, the present invention is explained in detail by Examples. But The following Examples are intended to further illustrate the present invention, and the scope of the Examples is not limited thereto.

EXAMPLE

Example 1

A crude alkylene oxide composition was obtained through a process of preparing an alkylene oxide. In such event, the crude compositions thus obtained contained $NH_4^+$, $NO_2^-$, and alkylene oxide.

100 g of the crude alkylene oxide composition was passed at a space velocity of 1 $h^{-1}$ through a container that contained 8 liters (about 6 kg) of a molecular sieve having an average diameter of about 2 mm and an average pore size of about 4 Å in a number per unit volume of about 20,000/liter, to thereby obtain a purified alkylene oxide composition.

Comparative Example 1

The same procedure as in Example 1 was repeated, except that the pore size of the molecular sieve was 10 Å.

Comparative Example 2

The same procedure as in Example 1 was repeated, except that the pore size of the molecular sieve was 2.3 Å.

EVALUATION EXAMPLE

The properties and post-processing results of the alkylene oxide compositions purified by the purification processes according to Example 1 and Comparative Examples 1 and 2 were evaluated. The results are shown in Table 1 below.

Evaluation Example 1: Measurement of the Content of $NH_4^+$

According to the test method of ASTM D 6919 (Standard Test Method for Determination of Dissolved Cation in Water by Ion Chromatography), 2 g of the composition to be measured was diluted with ultra-highly pure water, and $NH_4^+$ was quantitatively analyzed by an ion chromatography analyzer.

Evaluation Example 2: Measurement of the Content of $NO_2^-$

According to the test method of ASTM D 4327 (Standard Test Method for Anions in Water by Suppressed Ion Chromatography), 2 g of the composition to be measured was diluted with ultra-highly pure water, and $NO_2^-$ was quantitatively analyzed by an ion chromatography analyzer.

Evaluation Example 3: Measurement of CPR

According to the test method of ASTM D 6437 (Standard Test Method for Polyurethane Raw Materials), 30 g of the composition to be measured was mixed with 100 ml of methanol, followed by neutralization titration with 0.001N hydrochloric acid to calculate the amount of hydrochloric acid consumed.

Evaluation Example 4: Measurement of the Content of N

According to the test method of ASTM D 4629 (Standard Test Method for Trace Nitrogen in Liquid Hydrocarbons), 1 g of the composition to be measured was diluted with a highly pure solvent, which was burned in an oxygen and argon state to detect the wavelengths emitted by excited nitrogen dioxide for a quantitative analysis.

TABLE 1

|  |  | Ex. 1 | C. Ex. 1 | C. Ex. 2 |
|---|---|---|---|---|
| Crude alkylene oxide composition | Content of $NH_4^+$ | 1.05 ppm | 1.05 ppm | 1.05 ppm |
|  | Content of $NO_2^-$ | 0.55 ppm | 0.55 ppm | 0.55 ppm |
|  | CPR value | 1.0 | 1.0 | 1.0 |
|  | Content of N | 1.6 ppm | 1.6 ppm | 1.6 ppm |
| Purified alkylene oxide composition | Content of $NH_4^+$ | 0.55 ppm | Reaction terminated due to an exothermic reaction | 1.05 ppm |
|  | Content of $NO_2^-$ | 0.55 ppm |  | 0.55 ppm |
|  | CPR value | 0.1 |  | 1.0 |
|  | Content of N | 1.1 ppm |  | 1.6 ppm |

As can be seen from the above Table 1, the rate of improvement in the CPR was 90% or more, and the rate of reduction in the content of N was 30% or more in Example 1 as compared with Comparative Examples 1 and 2. Specifically, the test could not be carried out since an exothermic reaction took place in Comparative Example 1, and the CPR and the content of N were not improved in Comparative Example 2.

The invention claimed is:

1. A process for purifying an alkylene oxide composition, which comprises:
   (1) obtaining a crude alkylene oxide composition comprising an ionic component;
   (2) passing the crude alkylene oxide composition through a molecular sieve; and
   (3) obtaining a purified alkylene oxide composition,
   wherein the ionic component comprises a nitrogen-containing ionic component,
   wherein the crude alkylene oxide composition in the above step (1) has a controlled polymerization rate (CPR) of 0.2 to 20,
   wherein the CRP is a value measured according to the test method of ASTM D6437, and
   wherein 30 g of the crude alkylene oxide composition is mixed with 100 ml of methanol, and the amount of hydrochloric acid (concentration: 0.001 N) for neutralization titration is measured.

2. The process for purifying an alkylene oxide composition of claim 1,
   wherein the ionic component comprises a cationic component and an anionic component.

3. The process for purifying an alkylene oxide composition of claim 2,
   wherein the ionic component comprises 30 to 90% by weight of the cationic component based on the total weight of the ionic component.

4. The process for purifying an alkylene oxide composition of claim 1,
   wherein the nitrogen-containing ionic component comprises at least one selected from the group consisting of $NH_2^+$, $NH_4^+$, $NO_2^-$, and $NO_3^-$.

5. The process for purifying an alkylene oxide composition of claim 1,
   wherein the crude alkylene oxide composition in the above step (1) has a content of N of 0.2 to 10 ppm.

6. The process for purifying an alkylene oxide composition of claim 1,
   wherein the ionic component comprises $NH_4^+$, and
   the content of $NH_4^+$ contained in the crude alkylene oxide composition in the above step (1) is 0.1 to 5 ppm.

7. The process for purifying an alkylene oxide composition of claim 1,
   wherein the molecular sieve has a structure selected from the group consisting of zeolite A, zeolite X, zeolite beta, zeolite Y, zeolite L, and ZSM-12.

8. The process for purifying an alkylene oxide composition of claim 1,
   wherein the size of the pores of the molecular sieve is greater than 2.3 Å to less than 10 Å.

9. The process for purifying an alkylene oxide composition of claim 1,
   wherein the alkylene oxide is propylene oxide.

10. The process for purifying an alkylene oxide composition of claim 1,
    wherein the space velocity at which the crude alkylene oxide composition is passed through the molecular sieve is greater than 0 to 10 $h^{-1}$.

11. The process for purifying an alkylene oxide composition of claim 1,
    wherein the crude alkylene oxide composition is passed through a bead section after the step (1) and before the following step (2),
    the bead section comprises a plurality of beads having an average diameter of 1 to 5 mm, and
    the number of beads contained in the bead section per unit volume is 100 to 100,000/liter.

12. The process for purifying an alkylene oxide composition of claim 1,
    wherein the purified alkylene oxide composition comprises an ionic component that comprises a cationic component and an anionic component, and
    the ionic component comprises 10 to 70% by weight of the cationic component based on the total weight of the ionic component.

13. The process for purifying an alkylene oxide composition of claim 1,
wherein the purified alkylene oxide composition has a CPR of 0.2 to 2,
wherein the CPR is a value measured according to the test method of ASTM D6437, and
wherein 30 g of the purified alkylene oxide composition is mixed with 100 ml of methanol, and the amount of hydrochloric acid (concentration of 0.001 N) for neutralization titration is measured.

14. The process for purifying an alkylene oxide composition of claim 1,
wherein the purified alkylene oxide composition has a content of N of 0.1 to 5 ppm.

15. The process for purifying an alkylene oxide composition of claim 1,
wherein the purified alkylene oxide composition comprises $NH_4^+$, and
the content of $NH_4^+$ contained in the purified alkylene oxide composition is 0.05 to 2.5 ppm.

\* \* \* \* \*